(12) United States Patent
Ganter et al.

(10) Patent No.: US 10,398,478 B2
(45) Date of Patent: Sep. 3, 2019

(54) INTERSPINOUS STABILIZATION AND FUSION DEVICE

(71) Applicant: PARADIGM SPINE, LLC, New York, NY (US)

(72) Inventors: Detlev Ganter, Braunlingen (DE); Guntmar Eisen, Tuttlingen (DE); Stephan Eckhof, Reitheim-Weilheim (DE)

(73) Assignee: PARADIGM SPINE, LLC, New York, NY (US)

( * ) Notice: Subject to any disclaimer, the term of this patent is extended or adjusted under 35 U.S.C. 154(b) by 0 days.

(21) Appl. No.: 15/224,075

(22) Filed: Jul. 29, 2016

(65) Prior Publication Data
US 2017/0027619 A1    Feb. 2, 2017

Related U.S. Application Data

(60) Provisional application No. 62/199,433, filed on Jul. 31, 2015.

(51) Int. Cl.
*A61B 17/70* (2006.01)
(52) U.S. Cl.
CPC ...... *A61B 17/7065* (2013.01); *A61B 17/7062* (2013.01)
(58) Field of Classification Search
CPC ............ A61B 17/7062; A61B 17/7067; A61F 2/4405
See application file for complete search history.

(56) References Cited

U.S. PATENT DOCUMENTS

| 5,496,318 | A | 3/1996 | Howland et al. |
| 5,645,599 | A | 7/1997 | Samani |
| 6,440,169 | B1 | 8/2002 | Elberg et al. |
| 7,011,685 | B2 | 3/2006 | Amin et al. |
| 7,537,613 | B2 | 5/2009 | Amin et al. |
| 7,727,233 | B2 | 6/2010 | Blackwell et al. |
| 7,811,308 | B2 | 10/2010 | Amin et al. |
| 7,811,322 | B2 | 10/2010 | Amin et al. |
| 7,811,323 | B2 | 10/2010 | Amin et al. |
| 7,811,324 | B2 | 10/2010 | Amin et al. |
| 7,811,330 | B2 | 10/2010 | Amin et al. |
| 7,833,272 | B2 | 11/2010 | Amin et al. |

(Continued)

FOREIGN PATENT DOCUMENTS

| WO | 2009086397 A1 | 7/2009 |
| WO | 2010/025408 A2 | 3/2010 |
| WO | 2013123497 A1 | 8/2013 |

OTHER PUBLICATIONS

International Search Report and Written Opinion for PCT/US2016/044852 dated Oct. 17, 2016.

(Continued)

*Primary Examiner* — Julianna N Harvey
(74) *Attorney, Agent, or Firm* — Farber LLC; Tram Anh Nguyen

(57) ABSTRACT

An interspinous stabilization device configured to fit interlaminarly between adjacent vertebrae and their spinous processes, while also cooperating with a bone graft, or bone substitute, component to facilitate fusion at that segment of the spine is disclosed. Also provided is a method for using such a device and bone graft, or bone substitute, component to stabilize a spinal segment.

16 Claims, 4 Drawing Sheets

(56) References Cited

U.S. PATENT DOCUMENTS

| | | |
|---|---|---|
| 7,842,074 B2 | 11/2010 | Abdou |
| 7,842,090 B2 | 11/2010 | Amin et al. |
| 7,846,209 B2 | 12/2010 | Amin et al. |
| 7,862,590 B2 | 1/2011 | Lim et al. |
| 7,871,426 B2 | 1/2011 | Chin et al. |
| 8,002,802 B2 | 8/2011 | Abdou |
| 8,012,176 B2 | 9/2011 | Arnin et al. |
| 8,021,395 B2 | 9/2011 | Ben-Mokhtar et al. |
| 8,083,795 B2 | 12/2011 | Lange et al. |
| 8,206,420 B2 | 6/2012 | Patel et al. |
| 8,226,653 B2 | 7/2012 | Blackwell et al. |
| 8,236,031 B2 | 8/2012 | Bucci |
| 8,262,697 B2 | 9/2012 | Kirschman |
| 8,262,699 B2 | 9/2012 | Amin et al. |
| 8,303,629 B1 | 11/2012 | Abdou |
| 8,377,097 B2 | 2/2013 | Gordon et al. |
| 8,465,525 B2 | 6/2013 | Hawkins et al. |
| 8,568,453 B2 | 10/2013 | Abdou |
| 8,603,142 B2 | 12/2013 | Robinson |
| 8,603,143 B2 | 12/2013 | Robinson |
| 8,623,055 B2 | 1/2014 | Abdou |
| 8,636,773 B2 | 1/2014 | Stern et al. |
| 8,696,709 B2 | 4/2014 | Dinville et al. |
| 8,771,368 B2 | 7/2014 | McKay |
| 8,790,373 B2 | 7/2014 | Aflatoon |
| 8,876,866 B2 | 11/2014 | Lappacosta et al. |
| 8,906,065 B2 | 12/2014 | Robinson |
| 8,961,564 B2 | 2/2015 | Gordon et al. |
| 8,998,954 B2 | 4/2015 | Hartsell et al. |
| 9,066,760 B2 | 6/2015 | Taber et al. |
| 2005/0203624 A1 | 9/2005 | Serhan et al. |
| 2006/0015181 A1 | 1/2006 | Elberg |
| 2008/0009948 A1 | 1/2008 | Amin et al. |
| 2008/0281423 A1 | 11/2008 | Sheffer et al. |
| 2009/0005873 A1 | 1/2009 | Michael et al. |
| 2009/0270919 A1 | 10/2009 | Dos Reis, Jr. |
| 2009/0318967 A1 | 12/2009 | Jeon et al. |
| 2010/0049251 A1 | 2/2010 | Kuslich et al. |
| 2010/0280550 A1 | 11/2010 | Reo et al. |
| 2011/0029020 A1 | 2/2011 | Gordon et al. |
| 2011/0040330 A1 | 2/2011 | Sheffer |
| 2011/0184468 A1 | 7/2011 | Metcalf, Jr. et al. |
| 2011/0218572 A1 | 9/2011 | Lechmann et al. |
| 2011/0264221 A1 | 10/2011 | Woodward et al. |
| 2012/0004727 A1 | 1/2012 | Ben-Mokhtar et al. |
| 2012/0226312 A1* | 9/2012 | Thalgott ............ A61B 17/7062 606/246 |
| 2012/0303127 A1* | 11/2012 | Ullrich, Jr. ............ A61F 2/4455 623/17.16 |
| 2013/0184753 A1 | 7/2013 | Keiper et al. |
| 2013/0296939 A1 | 11/2013 | Perkins |
| 2013/0296940 A1 | 11/2013 | Northcutt et al. |
| 2013/0325065 A1 | 12/2013 | Malandain et al. |
| 2014/0005723 A1 | 1/2014 | Shah et al. |
| 2014/0074167 A1 | 3/2014 | Trautwein et al. |
| 2014/0107705 A1 | 4/2014 | Stern et al. |
| 2014/0114355 A1 | 4/2014 | Robinson |
| 2014/0121705 A1 | 5/2014 | Abdou |
| 2014/0228885 A1 | 8/2014 | Dinville et al. |
| 2014/0228886 A1 | 8/2014 | Aflatoon |
| 2014/0243898 A1 | 8/2014 | Fessler |
| 2014/0316466 A1 | 10/2014 | Dinville et al. |
| 2015/0012040 A1* | 1/2015 | Agarwal ............ A61B 17/7068 606/248 |
| 2015/0018887 A1 | 1/2015 | Zappacosta et al. |
| 2015/0025583 A1 | 1/2015 | Robinson |
| 2015/0112388 A1 | 4/2015 | Gordon et al. |

OTHER PUBLICATIONS

Extended Search Report for European Appl. No. 16833643.6 dated Mar. 14, 2019.

* cited by examiner

INTERSPINOUS STABILIZATION AND FUSION DEVICE

CROSS-REFERENCE TO RELATED APPLICATIONS

This application claims benefit of U.S. Provisional No. 62/199,433, filed Jul. 31, 2015, the entirety of which is herein incorporated by reference.

FIELD

The present disclosure relates to a device and method for treating spine instability, including an interspinous stabilization device for use with a bone graft, or graft substitute, component to facilitate fusion, and a method of using such a device for segmental stabilization of adjacent vertebrae.

BACKGROUND

Spinal instability is often attributed to undesirable excessive motion between vertebrae and can cause significant pain and morbidity. The instability may result from a number of causes, including abnormalities of the vertebrae, the intervertebral discs, the facet joints, and connective tissue around the spine. These abnormalities may arise from diseases, disorders or defects of the spine from trauma or bone degradation, such as osteoarthritis, or degenerative disc disease. When the spine becomes unstable, the vertebral column becomes misaligned and may produce micromotion between adjacent vertebrae. Vertebral misalignment and micromotion may result in wear to the vertebral bone surfaces and ultimately generate severe pain. These conditions are often chronic and create progressive problems for the sufferer.

Known treatments for spinal instability can include long-term medical management or surgery. Medical management is generally directed at controlling the symptoms, such as pain reduction, rather than correcting the underlying problem. For some patients, this may require chronic use of pain medications, which may alter the patient's mental state or cause other negative side effects. Surgical treatment typically includes decompression procedures to restore normal disc height, realign the column, and alleviate the pain.

Recently, a variety of interspinous vertebral devices have become available. These devices are typically implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering the anatomy of the spine.

These devices can be secured between adjacent spinous processes using a number of different mechanisms. For example, such devices can include sharp barbs or other surface projections that engage the bony surface of a spinous process. In addition, flexible ligaments or sutures can be placed around the implants and adjacent bone. In some cases, the devices may be rigidly attached to the spinous process using a bone screw or other suitable bone anchor to prevent the interspinous device from migrating or slipping out of position. When the device is fastened to the spinous process in this manner, the device allows for rigid, fusion promoting securement.

It is desirable to therefore provide a device that can fit interspinously and, more desirably, interlaminarly, between adjacent vertebrae to enhance the stability of the spine at that segment. It is further desirable to provide such devices with features that cooperate with a bone graft, or bone substitute, component to facilitate fusion for even stronger stabilization.

SUMMARY

The present disclosure provides an interspinous stabilization device configured to fit interlaminarly between adjacent vertebrae and their spinous processes, while also cooperating with a bone graft, or bone substitute, component to facilitate fusion at that segment of the spine. Also provided is a method for using such a device and bone graft, or bone substitute, component to stabilize a spinal segment.

According to one aspect of the disclosure, an interspinous stabilization and fusion device is provided. The device comprises a main body configured for interlaminar placement between adjacent vertebrae, the main body having a midsection, and an inferior section and superior section extending from the midsection to form a U-shaped body, each of the inferior and superior sections having a pair of lateral walls extending therefrom to form a stirrup for receiving a spinous process, the inferior and superior sections further having a cutout portion at their free ends to form a receiving slot, wherein each of the receiving slots includes one or more vertically extending teeth. The lateral walls may include apertures for receiving a bone fastener. In addition, the main body may include one or more horizontally extending ridges for enhancing bone attachment. These one or more horizontally extending ridges can be located on an external surface of the inferior and superior sections, and/or on the lateral walls. The gripping surface of each of the receiving slots may comprise a plurality of vertically extending teeth that are uniformly spaced apart, or they may be clustered in discreet regions in a pattern. In one embodiment, the receiving slot may be U-shaped.

According to another aspect of the disclosure, a spinal stabilization system is provided. The system can comprise an interspinous stabilization and fusion device, comprising a main body configured for interlaminar placement between adjacent vertebrae, the main body having a midsection, and an inferior section and superior section extending from the midsection to form a U-shaped body, each of the inferior and superior sections having a pair of lateral walls extending therefrom to form a stirrup for receiving a spinous process, the inferior and superior sections further having a cutout portion at their free ends to form a receiving slot, wherein each of the receiving slots includes one or more vertically extending teeth, and a bone fusion promoting component configured for placement inside the receiving slot. The lateral walls may further include apertures for receiving a bone fastener, and the system may further include a bone fastener for placement through the apertures of the lateral walls. In addition, the main body may include one or more horizontally extending ridges for enhancing bone attachment. These one or more horizontally extending ridges can be located on an external surface of the inferior and superior sections, and/or on the lateral walls. The gripping surface of each of the receiving slots may comprise a plurality of vertically extending teeth that are uniformly spaced apart, or they may be clustered in discreet regions in a pattern. In one embodiment, the receiving slot may be U-shaped.

In still another aspect of the disclosure, a method of stabilizing a spinal segment is provided. The method comprises the steps of selecting a vertebral level to be treated, positioning an interspinous stabilization and fusion device between two adjacent spinous processes of two adjacent vertebrae, the device comprising a main body configured for interlaminar placement between adjacent vertebrae, the main body having a midsection, and an inferior section and superior section extending from the midsection to form a U-shaped body, each of the inferior and superior sections having a pair of lateral walls extending therefrom to form a stirrup for receiving a spinous process, the inferior and superior sections further having a cutout portion at their free ends to form a receiving slot, wherein each of the receiving slots includes one or more vertically extending teeth, and placing a fusion promoting component, such as a bone graft or bone substitute component, into the receiving slots of the device. The method may further include the step of inserting a bone fastener through apertures on the lateral walls and spinous processes to secure the device to the vertebrae.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 3 represents a set of interspinous stabilization and fusion devices of FIG. 1 in increasing size, in which:

DETAILED DESCRIPTION OF THE EMBODIMENTS

Figure 1:
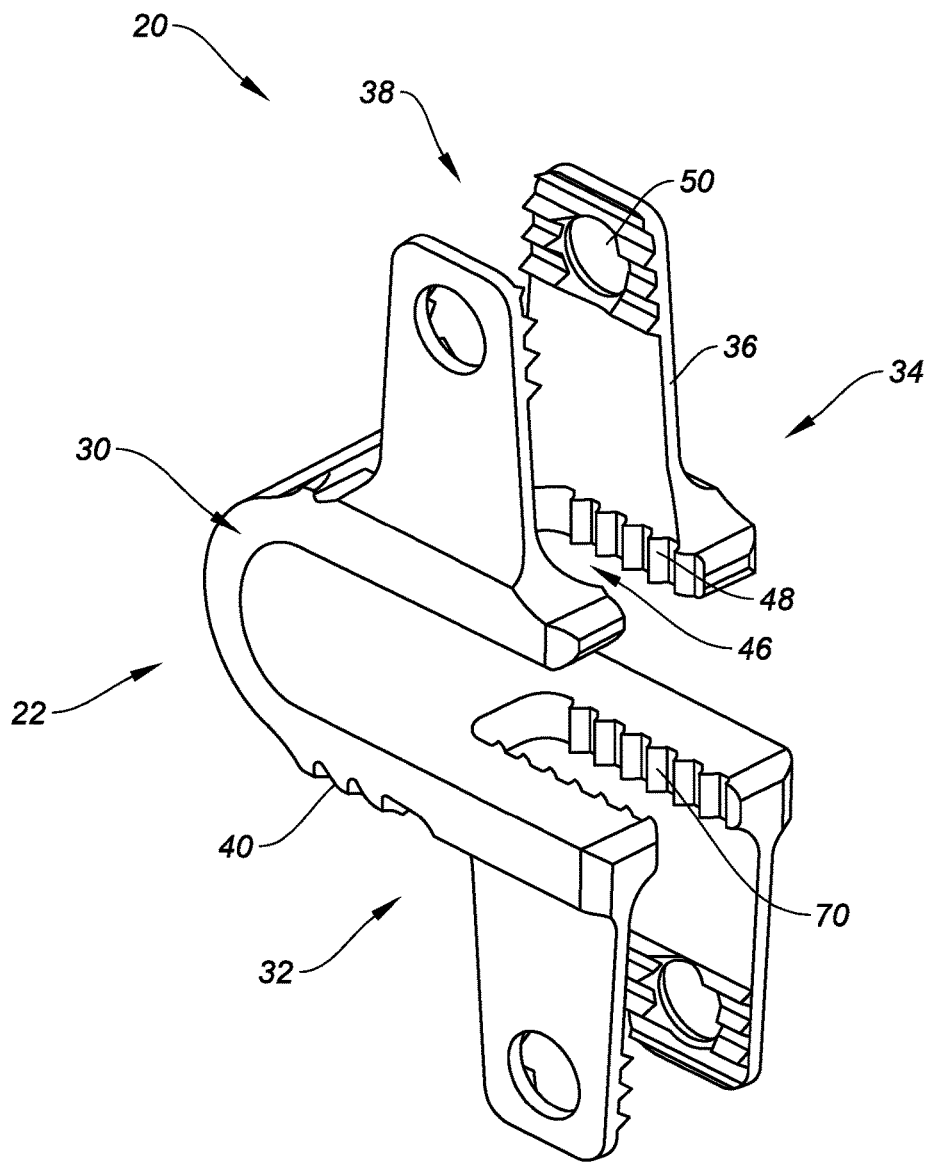
FIG. 1 shows a perspective view of an exemplary embodiment of an interspinous stabilization and fusion device of the present disclosure.

Turning now to the drawings, FIG. 1 illustrates an interspinous stabilization and fusion device 20 configured for placement between the spinous processes of adjacent vertebrae 2, 4 in accordance with an exemplary embodiment of the present disclosure. The interspinous device 20 may include a main body 22. The body 22 may have various shapes and thicknesses, and can be produced from a variety of different materials. In one embodiment, the body 22 may include a midsection 30 extending between an inferior section 32 and a superior section 34. When implanted in a patient, these sections serve as platforms such that the superior section 34 is configured to contact a portion of a first spinous process 6 of a first vertebra 2, while the inferior section 32 is configured to contact a portion of a second, adjacent spinous process 8 of a second, adjacent vertebra 4.

In one embodiment, the midsection 30, inferior section 32, and superior section 34 may together form a substantially U-shaped body 22, as shown. The body 22 may be configured to be flexible and/or bendable, such as, for example, by providing an extendable and/or compressible midsection 30. The midsection 30 can act as a flexible hinge, allowing the superior section 34 and inferior section 32 to move away from or towards one another. Furthermore, the U-shaped body 22 enables the device 20 to be positioned, or seated/fitted, interlaminarly after implantation, thereby enhancing the stabilization of the adjacent vertebrae by providing maximum surface-to-surface contact between the bones and the device.

Figures 2A, 2B:
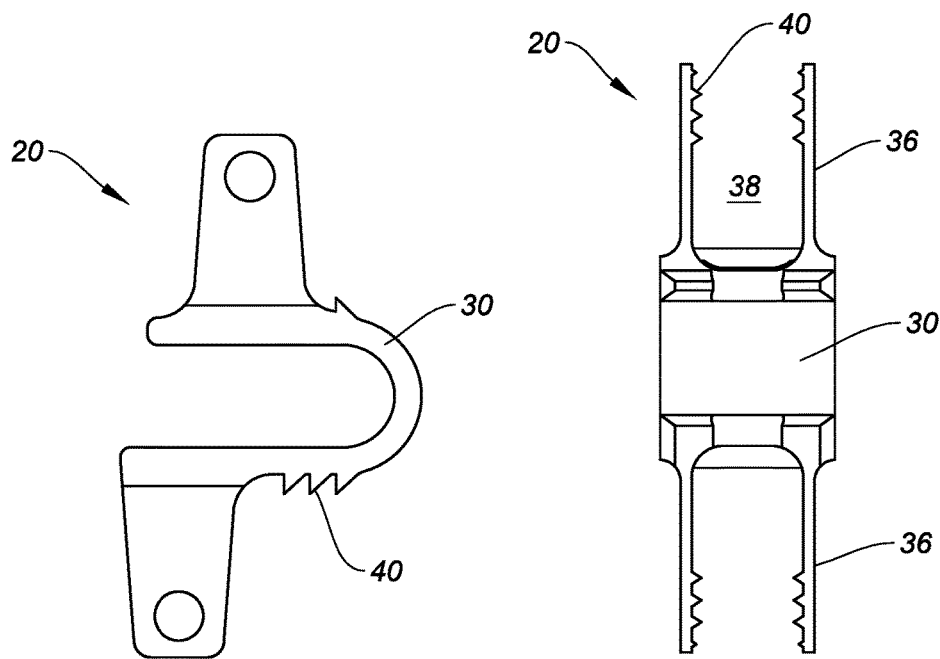
FIG. 2A is a side view of the interspinous stabilization and fusion device of FIG. 1.
FIG. 2B is a back view of the interspinous stabilization and fusion device of FIG. 1.
Figures 3A, 3B, 3C:
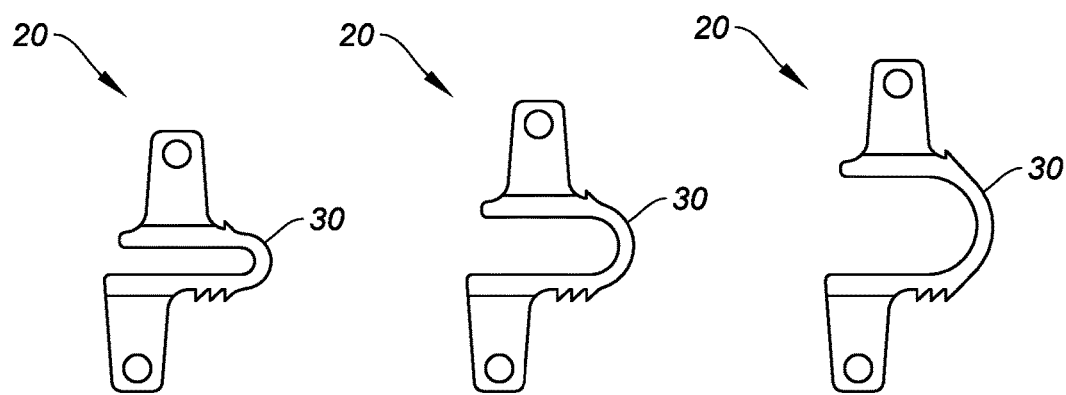
FIG. 3A is a relatively smaller sized device.
FIG. 3B is a relatively medium sized device.
FIG. 3C is a relatively larger sized device.

To engage the spinous processes of adjacent vertebrae, the main body 22 may be provided with a pair of lateral walls or brackets 36 that extend from the inferior and superior sections 32, 34, as shown in FIGS. 1 and 2B. Each of the pair of lateral walls 36 defines a stirrup 38 for receiving a spinous process. The body 22 can be provided with lateral walls 36 of various sizes or heights to accommodate variations in patient anatomy. For example, in one embodiment as shown in FIG. 3, a series of different sized devices 20 may be provided. The set of devices 20 may represent devices 20 in increasing size, and more specifically, increasing height of the midsection 30, among other dimensional differences. FIG. 3A illustrates a relatively smaller device 20 with a smaller midsection height, while FIG. 3B illustrates a relatively larger sized device 20 with a greater midsection height than that of the device 20 of FIG. 3A, and FIG. 3C illustrates an even larger sized device 20 with an even greater midsection height than that of the device of FIGS. 3A and 3B.

Likewise, the lateral walls 36 of different bodies 22 may be provided at differing locations along the length of the inferior section 32 or superior section 34. For example, as shown in FIGS. 1 and 2A, the pair of lateral walls 36 may be staggered so that stacking of the device 20 at different, adjacent levels of the spine is possible. The surgeon can thus select a suitably shaped and sized main body 22 depending on the particular vertebral level to be supported and the anatomy of the patient.

Further, the lateral walls 36 may also be adjustable with respect to the main body 22. For example, in one embodiment, the lateral walls 36 may be formed of a malleable material such that, after implantation, the surgeon may compress the lateral walls 36 together to reduce the gap between the lateral walls 36, thereby securely fixing the main body 22 to a spinous process seated therein. In addition, the lateral walls 36 may be spread apart to facilitate insertion. The lateral walls 36 may be compressed or spread apart, for example, using surgical pliers or forceps (not shown).

Although the interspinous device 20 is described and shown with superior and inferior lateral walls 36, the device 20 can also comprise a U-shaped implant with a single pair of lateral walls 36. Such devices may be used at the L5-S1 vertebral level. For example, the device 20 may include a single pair of lateral walls 36 configured to engage the spinous process and lamina of the L5 vertebra. Further, the device 20 may include a mechanism for securing the inferior section 32 to the sacrum.

A number of biocompatible materials are suitable for forming the main body 22 of the present disclosure. For example, in one embodiment, the main body 22 may be formed from a medical grade metal such as titanium or a titanium alloy. The main body 22 may also be formed from a variety of other materials, such as stainless steel, cobalt chrome, ceramics, and/or polymeric materials, such as ultra-high molecular-weight polyethylene (UHMWPE) and polyetheretherketone (PEEK), either alone or in combination with other suitable materials.

To further enhance the ability of the device 20 to be secured to the surrounding bone and soft tissue, the device 20 may include a number of surface modifications. For example, the main body 20 may include surface alterations that may facilitate tissue attachment, bonding, or fixation. These surface alterations may include protrusions, ridges, fins, teeth, barbs, beads, surface roughening, or the addition of bioactive agents to one or more sections of the device 20. For example, as illustrated, in one embodiment the device 20 may include one or more ridges 40 for securing the device 20 to bone and/or soft tissue. As shown, the ridges 40 may be located on the main body 22, such as on the external surface of the inferior section 32 and/or superior section 34. In some embodiments, the ridges 40 may extend in a generally horizontal direction. One ridge or a series of ridges 40 may be provided. Alternatively, or in addition, the ridges 40 may be located on an inner surface of the lateral walls 36. The ridges 40 may help the main body 22 securely engage connective tissue or a bony surface of a vertebra, such as the spinous process of the vertebra.

In other embodiments, the device 20 may also include roughened or porous surfaces. The roughened or porous surfaces may enhance attachment between implant surfaces and bone. In addition, some porous surfaces may facilitate tissue ingrowth to form a biological bond between sections of the device 20 and the surrounding bone and/or soft tissue. Roughened or porous surfaces may be included on any portion of the device 20.

The surface of the device 20 may also include biologically active agents. These agents may include osteogenic factors to further facilitate bonding between components of the device 20 and the surrounding bone and/or soft tissue. Further, the device 20 may include therapeutic agents such as antibiotics, steroids, anti-thrombotic agents, anti-inflammatory drugs, and/or analgesic agents. In one embodiment, the biologically active agent may be contained in a coating on the device 20. Alternatively, or in addition, the device 20 may be porous, and the biologically active agent may be contained in the pores of the device 20. The biologically active agent may be, for example, bone morphogenic protein (BMP) for modulating cartilage or bone growth.

Figure 2C:
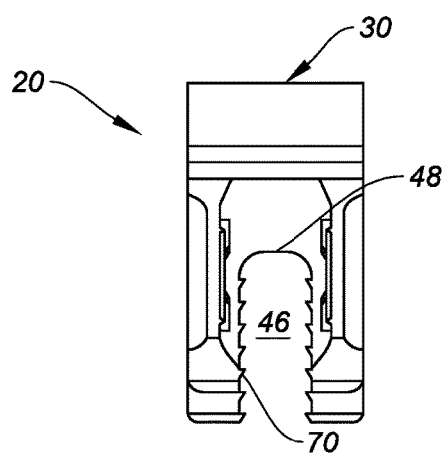
FIG. 2C is a top-down view of the interspinous stabilization and fusion device of FIG. 1.
Figure 4:
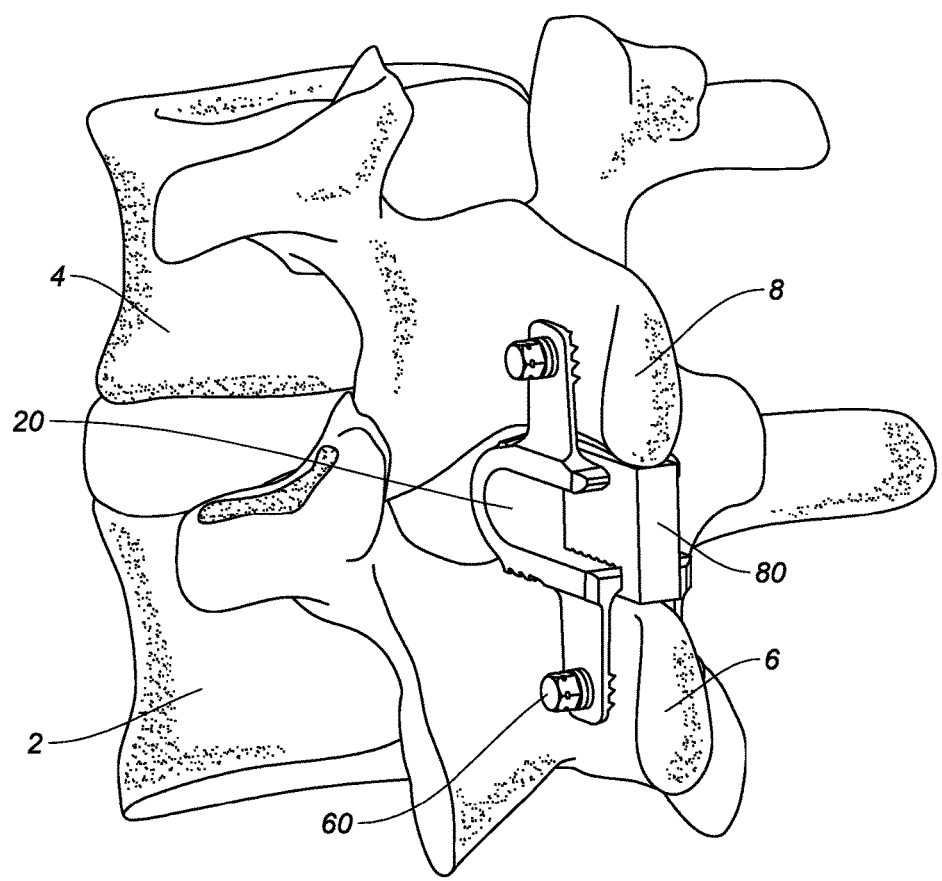
FIG. 4 shows the interspinous stabilization and fusion device of FIG. 1 in use with an exemplary bone graft, or bone substitute, component of the present disclosure in situ.

As previously mentioned, the interspinous device 20 may be used in cases where rigid stability of a spinal segment is desired. For example, in one exemplary embodiment, the device 20 may be configured as a fusion promoting device, and may include apertures 50 on the lateral walls 36 for receiving a bone fastener 60 such as a bone screw, ligament, band, tie, or other similar fastening mechanism to fix the brackets 36 to the spinous processes, as illustrated in FIG. 4. In addition, the inferior section 32 and superior section 34 may each include a slot or cutout portion 46 at their free ends so as to form a 3-sided, U-shaped wall 48 within each of the inferior and superior sections 32, 34, as shown in FIG. 2C. This U-shaped wall 48 serves as a receiving slot for holding a fusion promoting component 80, such as a bone graft, or graft substitute, as shown in FIG. 4. The body 22 may be configured to be rigid, i.e., not flexible and/or bendable, such as, for example, by providing an unextendable and/or uncompressible midsection 30. Such features enable rigid, fusion promoting securement of the device 20 to the adjacent vertebrae and their spinous processes.

In one exemplary embodiment, the fusion promoting component 80 may be shaped as a semi-solid or solid block that can be slid into the slots 46. The component 80 may be held by a friction fit or interference fit, or may be shaped to have a complementary fit with the shape of the receiving slots 46. In some embodiments, the slots 46 may have a gripping surface that comprises one or more vertically extending teeth 70 to hold the component 80 securely in position, and prevent slippage in the posterior direction. These one or more vertically extending teeth 70 may act to enhance the ability of the device 20 to retain the fusion promoting component 80, while also providing the device 20 with the ability to allow a ratcheting-like insertion of the fusion promoting component 80 into the receiving slots 46. That is, it is possible to adjust the placement depth of the fusion promoting component 80 by pushing the component 80 past one or more of these vertical teeth 70. As show the one or more vertically extending teeth 70 may be uniformly spaced. However, it is understood that the extending teeth 70 may also be non-uniformly spaced, or provided as a pattern such as a group of teeth 70 clustered in discreet regions along the gripping surface of the U-shaped slot 46.

In an exemplary embodiment of a method of treating a spinal instability of the present disclosure, the device 20 may be placed between adjacent vertebrae 2, 4 such that the spinous processes 6, 8 of the vertebrae are received within the stirrups 38 of the device 20. The device 20 is configured to seat interlaminarly as well as be interspinous, as shown. Bone fasteners 60 may be used to secure the device 20 to the vertebrae 2, 4 by securing the lateral walls 36 to the spinous processes 6, 8. After the device 20 is properly positioned and secured in place, a fusion promoting component 80, such as for example a bone graft plug or block, or bone substitute like putty or paste, may be inserted into the receiving slots 46 of the inferior and superior sections 32. The device 20 and the fusion promoting component 80 work in tandem to support and stabilize the spinal segment, providing rigid fixation of the vertebrae together.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An interspinous stabilization and fusion device, comprising:
a main body configured for interlaminar placement between adjacent vertebrae, the main body having a midsection, and an inferior section and superior section extending from the midsection to form a U-shaped body, each of the inferior and superior sections having a pair of lateral walls extending therefrom to form a stirrup for receiving a spinous process, each of the inferior and superior sections further having a U-shaped cutout portion to form a receiving slot having three walls formed around an opening, the opening facing the posterior direction, wherein each of the receiving slots includes a gripping surface comprising one or more vertically extending teeth on a pair of opposed walls, the vertically extending teeth of the receiving slot of the superior section being vertically aligned with the vertically extending teeth of the receiving slot of the inferior section, wherein the teeth are configured to enable ratcheting, adjustable depth placement of a fusion promoting component within the receiving slots.

2. The device of claim 1, wherein the lateral walls include apertures for receiving a bone fastener.

3. The device of claim 1, wherein the main body includes one or more horizontally extending ridges for enhancing bone attachment.

4. The device of claim 3, wherein the one or more horizontally extending ridges are located on an external surface of the inferior and superior sections.

5. The device of claim 3, wherein the one or more horizontally extending ridges are located on the lateral walls.

6. The device of claim 1, wherein the gripping surface of each of the receiving slots comprises a plurality of vertically extending teeth that are uniformly spaced apart.

7. A spinal stabilization system, comprising:
an interspinous stabilization and fusion device, comprising a main body configured for interlaminar placement between adjacent vertebrae, the main body having a midsection, and an inferior section and superior section extending from the midsection to form a U-shaped body, each of the inferior and superior sections having a pair of lateral walls extending therefrom to form a stirrup for receiving a spinous process, each of the inferior and superior sections further having a U-shaped cutout portion to form a receiving slot having three walls formed around an opening, the opening facing the posterior direction; and
a bone fusion promoting component configured for placement inside the receiving slot;
wherein each of the receiving slots include a gripping surface comprising one or more vertically extending teeth on a pair of opposed walls, the vertically extending teeth of the receiving slot of the superior section being vertically aligned with the vertically extending teeth of the receiving slot of the inferior section, wherein the teeth are configured to enable ratcheting, adjustable depth placement of the fusion promoting component within the receiving slots and being configured to prevent posterior movement of the bone fusion promoting component.

8. The system of claim 7, wherein the lateral walls further include apertures for receiving a bone fastener.

9. The system of claim 8, further including a bone fastener for placement through the apertures of the lateral walls.

10. The system of claim 7, wherein the main body includes one or more horizontally extending ridges for enhancing bone attachment.

11. The system of claim 10, wherein the one or more horizontally extending ridges are located on an external surface of the inferior and superior sections.

12. The system of claim 10, wherein the one or more horizontally extending ridges are located on the lateral walls.

13. The system of claim 7, wherein the gripping surface of each of the receiving slots comprises a plurality of vertically extending teeth that are uniformly spaced apart.

14. A method of stabilizing a spinal segment, comprising:
selecting a vertebral level to be treated;
positioning an interspinous stabilization and fusion device between two adjacent spinous processes of two adjacent vertebrae, the device comprising a main body configured for interlaminar placement between adjacent vertebrae, the main body having a midsection, and an inferior section and superior section extending from the midsection to form a U-shaped body, each of the inferior and superior sections having a pair of lateral walls extending therefrom to form a stirrup for receiving a spinous process, each of the inferior and superior sections further having a U-shaped cutout portion to form a receiving slot having three walls formed around an opening, the opening facing the posterior direction, wherein each of the receiving slots includes a gripping surface comprising one or more vertically extending teeth on a pair of opposed walls, the vertically extending teeth of the receiving slot of the superior section being vertically aligned with the vertically extending teeth of the receiving slot of the inferior section, wherein the teeth are configured to enable ratcheting, adjustable depth placement of a fusion promoting component within the receiving slots; and
placing the fusion promoting component into the receiving slots of the device.

15. The method of claim 14, further including the step of inserting a bone fastener through apertures on the lateral walls and spinous processes to secure the device to the vertebrae.

16. The method of claim 14, wherein the fusion promoting component comprises a bone graft or bone substitute component.

* * * * *